(12) United States Patent
Ide

(10) Patent No.: US 12,379,510 B2
(45) Date of Patent: Aug. 5, 2025

(54) RADIATION DETECTOR AND RADIATION IMAGE CAPTURING SYSTEM

(71) Applicant: CANON KABUSHIKI KAISHA, Tokyo (JP)

(72) Inventor: Kunihito Ide, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 205 days.

(21) Appl. No.: 18/314,934

(22) Filed: May 10, 2023

(65) Prior Publication Data
US 2023/0375728 A1 Nov. 23, 2023

(30) Foreign Application Priority Data

May 17, 2022 (JP) .................. 2022-080622
Mar. 2, 2023 (JP) .................. 2023-031514

(51) Int. Cl.
*G01T 1/24* (2006.01)
*A61B 6/42* (2024.01)

(52) U.S. Cl.
CPC .............. *G01T 1/24* (2013.01); *A61B 6/4208* (2013.01)

(58) Field of Classification Search
CPC .................. G01T 1/24; A61B 6/4206
See application file for complete search history.

(56) References Cited

U.S. PATENT DOCUMENTS

| 5,345,107 A | 9/1994 | Daikoku et al. |
| 11,011,558 B2 | 5/2021 | Sakaguchi et al. |
| 11,417,498 B2 | 8/2022 | Janssen et al. |
| 2005/0258550 A1* | 11/2005 | Morita ............... H05K 1/0271 257/784 |
| 2006/0067373 A1* | 3/2006 | Alander ............... H01S 5/4031 372/34 |
| 2013/0286565 A1* | 10/2013 | Tsuduki ............... H01L 23/10 361/679.01 |

FOREIGN PATENT DOCUMENTS

| JP | 1-303745 A | 12/1989 |
| JP | 2-168658 A | 6/1990 |
| JP | 2019-87640 A | 6/2019 |
| JP | 2021-18988 A | 2/2021 |

* cited by examiner

*Primary Examiner* — Hugh Maupin
(74) *Attorney, Agent, or Firm* — Venable LLP

(57) ABSTRACT

A radiation detector includes a semiconductor layer, a circuit board, and a heat conduction member. A first area in which the semiconductor layer and the heat conduction member overlap each other in this order, and the circuit board does not overlap, and a second area in which the semiconductor layer, the circuit board, and the heat conduction member overlap each other in this order are provided adjacent to each other in a case where the radiation detector is seen through from a direction perpendicular to a main surface of the semiconductor layer. The first area is provided with a space separating the semiconductor layer and the heat conduction member in the direction perpendicular to the main surface at a boundary portion with the second area.

14 Claims, 14 Drawing Sheets

RADIATION DETECTOR AND RADIATION IMAGE CAPTURING SYSTEM

BACKGROUND OF THE INVENTION

Field of the Invention

The present invention relates to a radiation detector.

Description of the Related Art

There is known a radiation detector that obtains a radiation image by receiving radiation with a semiconductor element such as a CMOS image sensor without using a scintillator (wavelength converter). In such a radiation detector, when radiation enters a deep part of the semiconductor element, crosstalk or secondary electrons are generated to reduce detection accuracy, and thus a semiconductor layer is thinned.

Japanese Patent Laid-Open No. 2019-87640 A discloses a detector in which a thickness of a semiconductor layer in at least a part of a detection area is smaller than a thickness of a peripheral area.

Japanese Patent Laid-Open No. 2021-18988 A discloses that when a charged particle detector including a sensitive layer, a mechanical support layer, and a substrate layer is manufactured, a step of thinning the substrate layer is performed after the mechanical support layer is connected to an opposite side of the substrate layer with the sensitive layer interposed therebetween.

In such a radiation detector, the semiconductor element is cooled in order to suppress generation of noise.

Japanese Patent Laid-Open No. H02-168658 A discloses a cooling device of an electronic device in which a large number of grooves are formed on a heat transfer surface of the electronic device or a cooling body, and the grooves communicate with a space around the heat transfer surface.

Japanese Patent Laid-Open No. H01-303745 A discloses a package of a solid-state imaging element to which a thermal conductor having excellent thermal conductivity is connected.

If the semiconductor layer is thinned, generation of the crosstalk and the secondary electrons may be reduced, but the mechanical strength of the semiconductor element is reduced. In general, other members are disposed around the semiconductor element so as to be in contact with the semiconductor element. However, if the semiconductor element is cooled when the radiation detector is used for noise reduction, these members around the semiconductor element are also cooled. Then, uneven deformation occurs in the device due to a difference in linear expansion coefficient between the semiconductor element and the member around the semiconductor element. However, if an excessive force is applied due to the deformation, the semiconductor element having low mechanical strength may be damaged.

Therefore, there is need for a radiation detector that can obtain a radiation image with high image quality without being damaged even when the semiconductor element is cooled.

SUMMARY OF THE INVENTION

According to a first aspect of the present invention, a radiation detector includes a semiconductor layer, a circuit board, and a heat conduction member. A first area in which the semiconductor layer and the heat conduction member overlap each other in this order, and the circuit board does not overlap, and a second area in which the semiconductor layer, the circuit board, and the heat conduction member overlap each other in this order are provided adjacent to each other in a case where the radiation detector is seen through from a direction perpendicular to a main surface of the semiconductor layer. The first area is provided with a space separating the semiconductor layer and the heat conduction member in the direction perpendicular to the main surface at a boundary portion with the second area. A height of the space in the direction perpendicular to the main surface of the semiconductor layer is larger than a thickness of the circuit board.

Further features of the present invention will become apparent from the following description of exemplary embodiments with reference to the attached drawings.

DESCRIPTION OF THE EMBODIMENTS

Figure 1A:
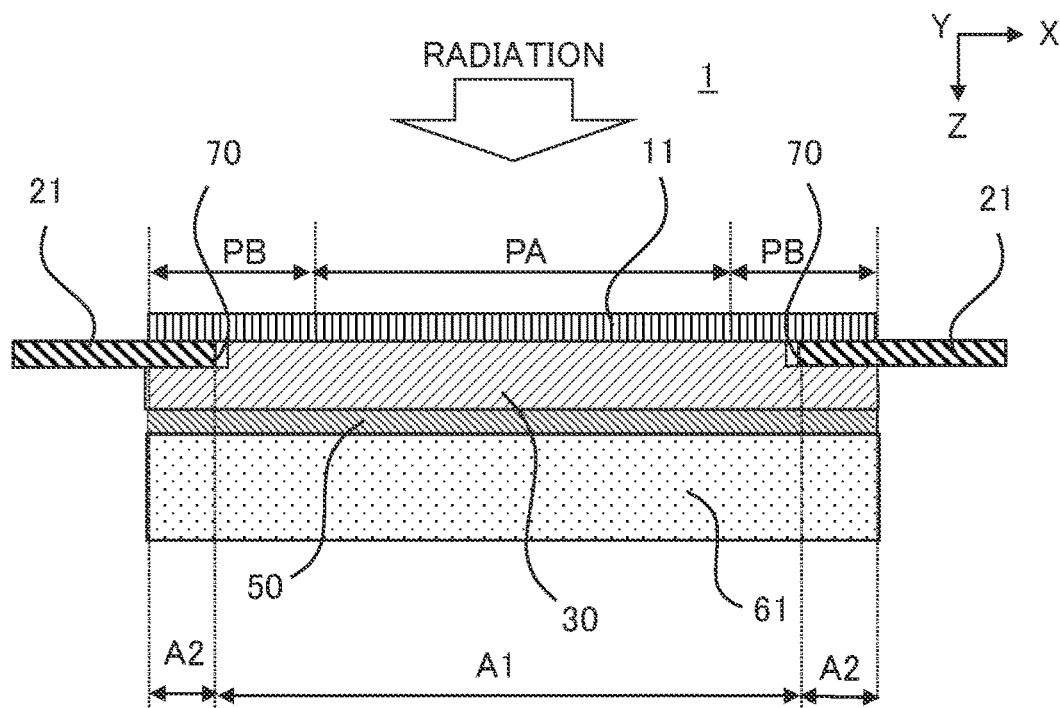
FIG. 1A is a cross-sectional view of a radiation detector 1 according to Embodiment 1.

Radiation detectors according to embodiments of the present invention are described with reference to the drawings. The embodiments described below are examples, and for example, detailed configurations can be appropriately changed and implemented by those skilled in the art without departing from the gist of the present invention.

Further, in the drawings referred to in the following description, elements denoted by the same reference numerals have the same functions unless otherwise specified. In addition, since the drawings may be schematically represented for convenience of illustration and description, the drawings do not strictly coincide with the shape, size, arrangement, and the like of the actual object.

The radiation detected by the radiation detector according to the embodiment may be an electromagnetic wave or a particle beam. The electromagnetic wave may be a light ray such as an infrared ray, a visible ray, or an ultraviolet ray, may be a radio wave such as a microwave, or may be ionizing radiation such as an X-ray or a gamma ray. Examples of the particle beam include an alpha beam, a beta beam, an electron beam, a neutron beam, a proton beam, a heavy ion beam, and a meson beam. The structure of the radiation detector, for example, the thickness of the semiconductor layer that converts the radiation into an electrical signal may be appropriately set according to the transmission characteristics and absorption characteristics of the radiation to be detected.

Embodiment 1

Figure 1B:
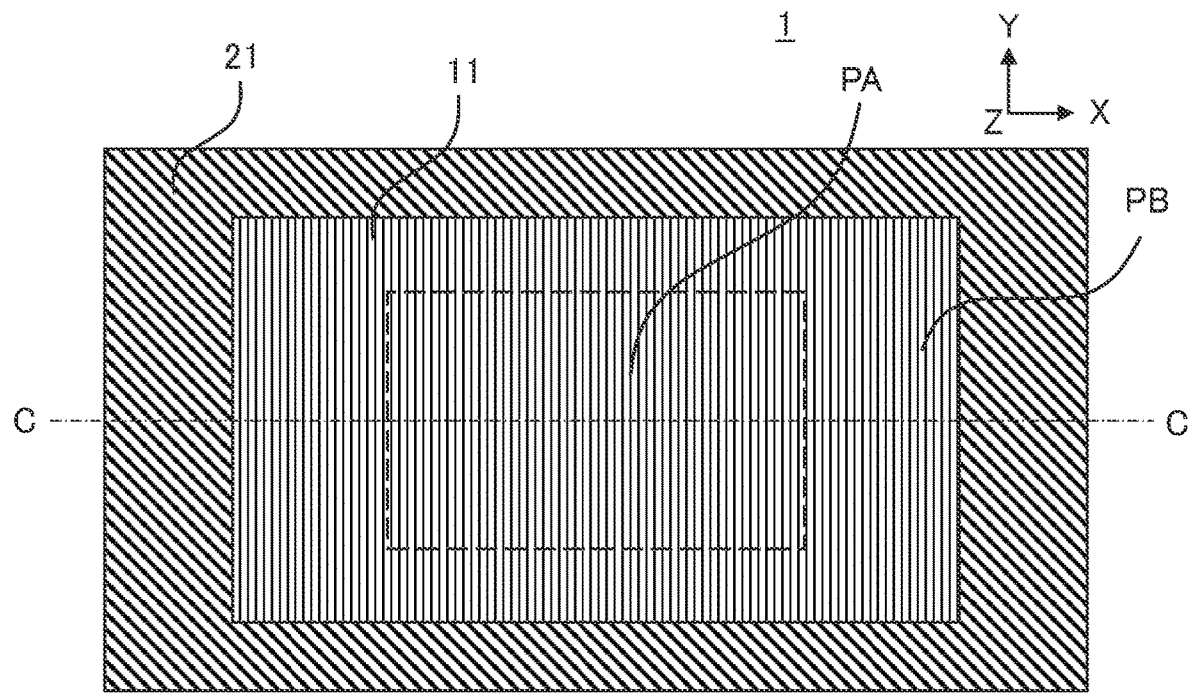
FIG. 1B is a plan view of the radiation detector 1 according to Embodiment 1.
Figure 2:
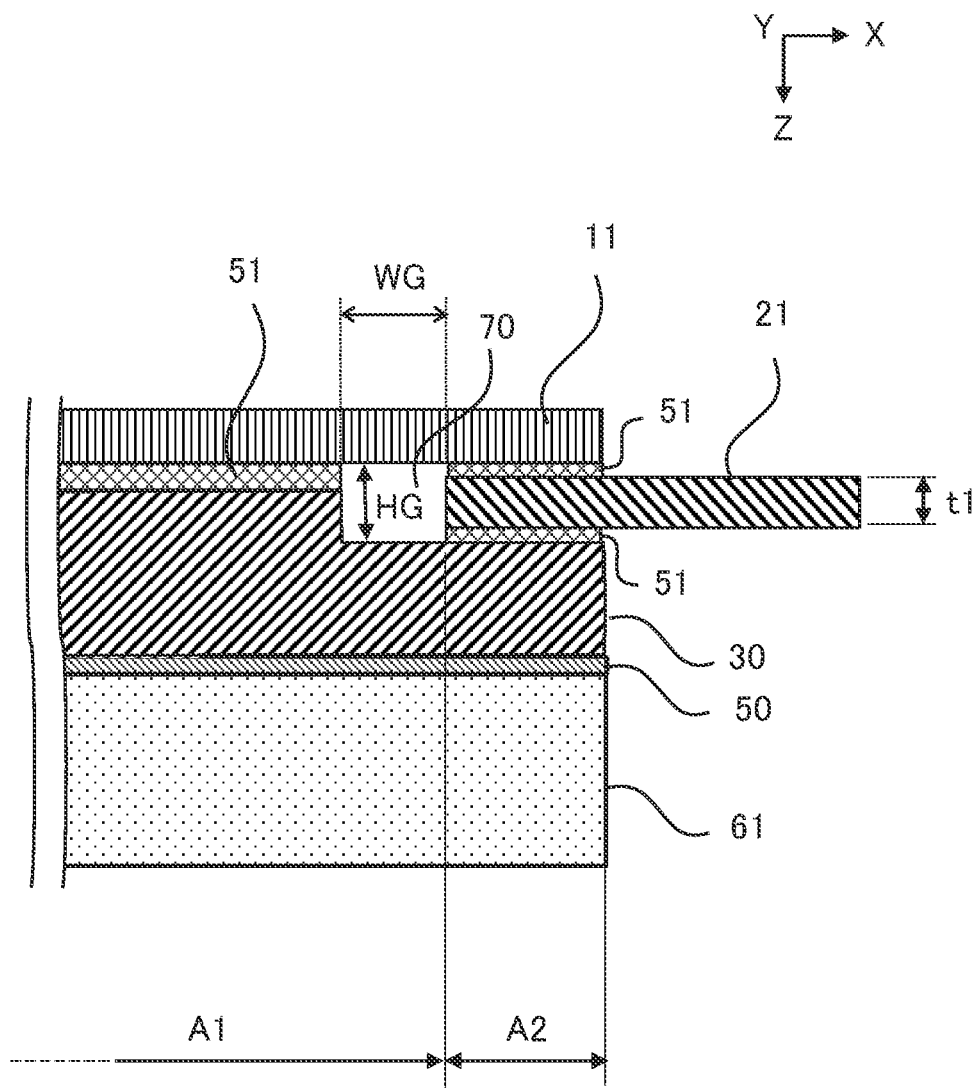
FIG. 2 is a partially enlarged view of a right side part of FIG. 1A.

A plan view of the radiation detector 1 according to the present embodiment as viewed from a direction in which radiation is incident is illustrated in FIG. 1B, and a cross section taken along line C-C of FIG. 1B is illustrated in FIG. 1A. In addition, FIG. 2 illustrates a partially enlarged view of a right side part of FIG. 1A. The radiation detector 1 includes a semiconductor layer 11, a circuit board 21, a heat conduction member 30, and a cooling device 61.

The semiconductor layer 11 is formed with a single crystal layer of silicon, germanium, or the like, or a polycrystalline layer and includes a detection area PA as a light receiving unit and a peripheral area PB. The peripheral area PB, which has a frame shape surrounding the detection area PA in FIG. 1B, is an area other than the detection area PA.

The detection area PA as a light receiving unit is an area provided with a mechanism for converting electrons generated by incidence of radiation into an output signal and has a structure in which a plurality of pixels and reading circuits for forming an image based on radiation are arranged in a matrix. The light receiving unit may be said to be an area on which radiation is incident or may also be said to be a detection unit. Each of the plurality of pixels can include a photodiode, similarly to a CMOS image sensor or a CCD. As the photodiode, a compound semiconductor such as cadmium telluride (CdTe) or cadmium zinc telluride (CdZnTe) may be used. In addition, a photon counting principle may be used, and a device such as a single photon avalanche diode (SPAD) may be used.

In the detection area PA, similarly to the CMOS image sensor and the CCD, a circuit of a system of transferring electrons accumulated in the photodiode to the floating diffusion layer via the transfer transistor and reading the potential via a source follower can be provided. A circuit of a system in which the potential of an accumulation unit is directly set to a gate potential of the source follower may be provided without using a transfer transistor.

The peripheral area PB is provided with peripheral circuits such as a drive circuit, a control circuit, a signal processing circuit, and an output circuit, an input terminal, and an output terminal. The drive circuit is a circuit that scans and drives the reading circuit of each pixel in the detection area PA. The control circuit is a circuit that controls drive timing of the drive circuit, the signal processing circuit, and the like and includes a timing generator and the like. The signal processing circuit processes a signal read from the reading circuit of the detection area PA and includes an amplifier circuit and an AD conversion circuit. The output circuit converts a signal obtained by the signal processing circuit into a predetermined format and outputs the converted signal, and includes a differential transmission circuit. The input terminal is a terminal to which a power supply or a control signal is input from the outside, and the output terminal is a terminal to output a signal to the outside.

The semiconductor layer 11 may be a substrate having a uniform thickness as illustrated in FIG. 1A but may be configured such that a thickness of the detection area PA is smaller than a thickness of the peripheral area PB in order to suppress generation of crosstalk and secondary electrons. In this case, a single substrate may be processed so as to reduce the thickness of the part of the detection area PA, or the thickness of the semiconductor layer in the peripheral area may be increased by bonding another substrate to a peripheral area of a substrate having a small thickness. In addition, a plurality of substrates may be bonded by a known method, and then a process of thinning a part corresponding to the detection area PA may be performed. For example, if CdTe or CdZnTe is used as a photodiode, the signal reading circuit unit may be configured with a separately produced CMOS or the like, and the photodiode and the circuit unit may be boned to each other by solder or the like to produce the semiconductor layer 11. The thickness of the detection area PA is preferably 10 μm to 100 μm and desirably 25 μm to 75 μm in consideration of a balance between prevention of the crosstalk and securing of mechanical strength. Typically, the thickness is set to 50 μm.

In the semiconductor layer 11, assuming that a main surface on the radiation incident side is referred to as a front surface, and a main surface on the opposite side is referred to as a back surface, a first area A1 including the detection area PA and a part of the peripheral area PB on the back surface faces the heat conduction member 30. A second area A2 including the remaining part of the peripheral area PB on the back surface faces the circuit board 21.

Although not illustrated in FIG. 1A for convenience of illustration, as can be seen with reference to FIG. 2, in the first area A1 where the back surface of the semiconductor layer 11 and the heat conduction member 30 face each other, the back surface of the semiconductor layer 11 and the heat conduction member 30 are bonded to each other by an adhesive layer 51 except for a part corresponding to a space 70. In the second area A2 where the back surface of the semiconductor layer 11 and the circuit board 21 face each other, the back surface of the semiconductor layer 11 and the circuit board 21 are bonded to each other by the adhesive layer 51. For the adhesive layer 51, an adhesive is used, but in some cases, a die attach film (DAF), a double-sided tape, or the like may be used. Note that, in the first area A1, the semiconductor layer 11 and the heat conduction member 30 may be bonded to each other by the adhesive layer 51 on all the facing surfaces except for the part corresponding to the space 70 as illustrated in the drawing, may be bonded to each other only in a part of the first area A1 except for the part corresponding to the space 70, or may not be bonded to each other by the adhesive layer 51. Also, in the second area A2, the semiconductor layer 11 and the circuit board 21 may be bonded to each other by the adhesive layer 51 on all the facing surfaces as illustrated in the drawing, may be bonded to each other by the adhesive layer 51 only in a part of the second area A2, or may not be bonded to each other by the adhesive layer 51. In addition, in the second area A2, the circuit board 21 and the heat conduction member 30 may not be bonded to each other by the adhesive layer 51 on all the facing surfaces, or may be bonded to each other by the adhesive layer 51 in at least a part of the second area A2.

The circuit board 21 is a substrate on which an electric circuit that achieves functions of supplying a control signal and power to a radiation detection sensor provided in the semiconductor layer 11, processing a signal output from the semiconductor layer 11, storing a signal, transmitting the signal to an external computer or a network, and the like is mounted. Although the circuit board 21 and the input terminal and the output terminal of the semiconductor layer 11 are electrically connected via wire bonding (not illustrated), the circuit board 21 and the semiconductor layer 11 may be electrically connected by a method other than the wire bonding.

The heat conduction member 30 is a member for effectively transmitting heat of the semiconductor layer 11 and the circuit board 21 to the cooling device 61, and for example, a material having a high thermal conductivity such as Mo, CuW, CuMo, Si, SiC, SiN, AlN, $Al_2O_3$, or synthetic diamond is suitably used. The heat conduction member 30 is connected to the cooling device 61 by a buffer member 50. The buffer member 50 is made of a material that can be easily separated and has a good thermal conductivity, such as a pseudoplastic fluid, a plastic fluid, or a double-sided tape. This is because, when the semiconductor layer 11 deteriorates and needs to be exchanged, the semiconductor layer 11, the circuit board 21, and the heat conduction member 30 are set as a unit and are conveniently exchanged on a unit basis.

The cooling device 61 is a heat-exchangeable device such as a Peltier element or a liquid-cooled pipe. The cooling device 61 exhausts heat generated in the semiconductor layer 11 and the circuit board 21 via the heat conduction member 30. In particular, a dark current of the detection unit, which becomes noise, is reduced by cooling the semiconductor layer 11, so that highly accurate detection data (radiation image data) can be obtained.

As illustrated in FIG. 1A, in the present embodiment, a space 70 that separates the semiconductor layer 11 and the heat conduction member 30 is provided at a boundary portion with the second area A2 in the first area A1. As illustrated in FIG. 2, a height HG of the space 70 is larger than a thickness t1 of the circuit board 21 in a direction perpendicular to the main surface of the semiconductor layer 11 (Z direction). In a direction parallel to the main surface of the semiconductor layer 11 (X direction), a width WG of the space 70 is set to 20 μm or more in a state where the radiation detector 1 is placed at normal temperature. Unless specifically stated otherwise, the description relating to the shape and dimensions of the space 70 is in a state where the radiation detector 1 is placed in a normal temperature environment, and there is no substantial temperature difference among the semiconductor layer 11, the circuit board 21, and the heat conduction member 30.

That is, when the radiation detector 1 is seen through from the direction perpendicular to the main surface of the semiconductor layer 11 (Z direction), the first area A1 in which the semiconductor layer 11 and the heat conduction member 30 overlap in this order, and the circuit board 21 does not overlap, and the second area A2 in which the semiconductor layer 11, the circuit board 21, and the heat conduction member 30 overlap in this order are provided adjacent to each other. In the first area A1, the space 70 is provided at the boundary portion with the second area A2. The space 70 can separate the semiconductor layer 11 from the heat conduction member 30 in the Z direction. In the space 70, the height HG in the direction perpendicular to the main surface of the semiconductor layer 11 (Z direction) is larger than the thickness t1 of the circuit board 21. In addition, the space 70 can separate the circuit board 21 and the heat conduction member 30 in the X direction. Note that a case where the radiation detector 1 is seen through from the direction perpendicular to the main surface of the semiconductor layer 11 (Z direction) is also referred to as a case where the radiation detector 1 is viewed in a plan view.

The radiation detector 1 is assembled in a room temperature environment at the time of production, but is cooled to a temperature lower than room temperature by the cooling device 61 at the time of use. Generally, the semiconductor layer 11, the heat conduction member 30, and the circuit board 21 are made of materials having different linear expansion coefficients and thus have different thermal shrinkage amounts. For example, if the semiconductor layer 11 is silicon, the heat conduction member 30 is Mo, and the circuit board 21 is FR-4 of a general multilayer printed wiring board, the linear expansion coefficients are 3.9E−6/K, 5.2E−6/K, and 14E−6/K, respectively.

Assuming that the circuit board 21 and the heat conduction member 30 are assembled in a state of being in contact with each other in the X direction, if the linear expansion coefficient of the circuit board 21 is larger than the linear expansion coefficient of the heat conduction member 30 as in the above example, a disadvantage occurs when the circuit board 21 and the heat conduction member 30 are cooled. That is, the circuit board 21 tends to contract more than the heat conduction member 30 contracts along a main surface direction due to the difference in the linear expansion coefficient but cannot contract along the main surface direction if the circuit board 21 is in contact with the heat conduction member 30 so as to surround the heat conduction member 30. Therefore, warpage or distortion occurs in the circuit board 21. When warpage or distortion occurs in the circuit board 21, a force is applied to the semiconductor layer 11 in contact with the upper surface of the circuit board 21, but the semiconductor layer 11 may be damaged due to the small thickness thereof.

On the other hand, according to the present embodiment, the space 70 is provided between the circuit board 21 and the heat conduction member 30, the height HG of the space 70 is larger than the thickness t1 of the circuit board 21, and the width WG of the space 70 is 20 μm or more. For this reason, even if the linear expansion coefficient of the circuit board 21 is larger than the linear expansion coefficient of the heat conduction member 30, the circuit board 21 that tends to contract in the main surface direction when cooled below the normal temperature is not in contact with the heat conduction member 30, or the force applied therebetween can be reduced. That is, warpage or distortion does not occur in the circuit board 21. Therefore, the semiconductor layer 11 having a small thickness is prevented from being damaged. Note that, although the XZ cross section is illustrated in FIG. 1A, it is desirable to similarly provide the space 70 also in the YZ cross section. That is, it is desirable to provide the space 70 so as to surround the outer side of the detection area PA in plan view.

For example, in a case where the temperature at the time of assembly is 25° C., the temperature when cooled at the time of radiation detection is −20° C., and the length of the first area A1 is 25 mm, the circuit board 21 tends to contract more than the heat conduction member 30 by 9.9 μm as in the following calculation.

25 mm×(25° C.−(−20° C.))×((14$E$−6)−(5.2$E$−6))= 0.0099 mm=9.9 μm

In the present embodiment, the width WG of the space 70 is set to 20 μm or more in consideration of the deviation from the set temperature at the time of cooling, the shape accuracy of the member, and the like. Therefore, a sufficient clearance is secured between the circuit board 21 and the heat conduction member 30, and the semiconductor layer 11 having a small thickness is prevented from being damaged due to warpage or distortion of the circuit board 21. That is, it is possible to realize the radiation detector 1 that can obtain a radiation image with high image quality without being damaged even if the semiconductor element is cooled during use. In order to prevent the radiation from colliding with air and scattering, the radiation detector 1 may be operated in vacuum or under an environment of low atmospheric pressure.

Embodiment 2

Figure 3:
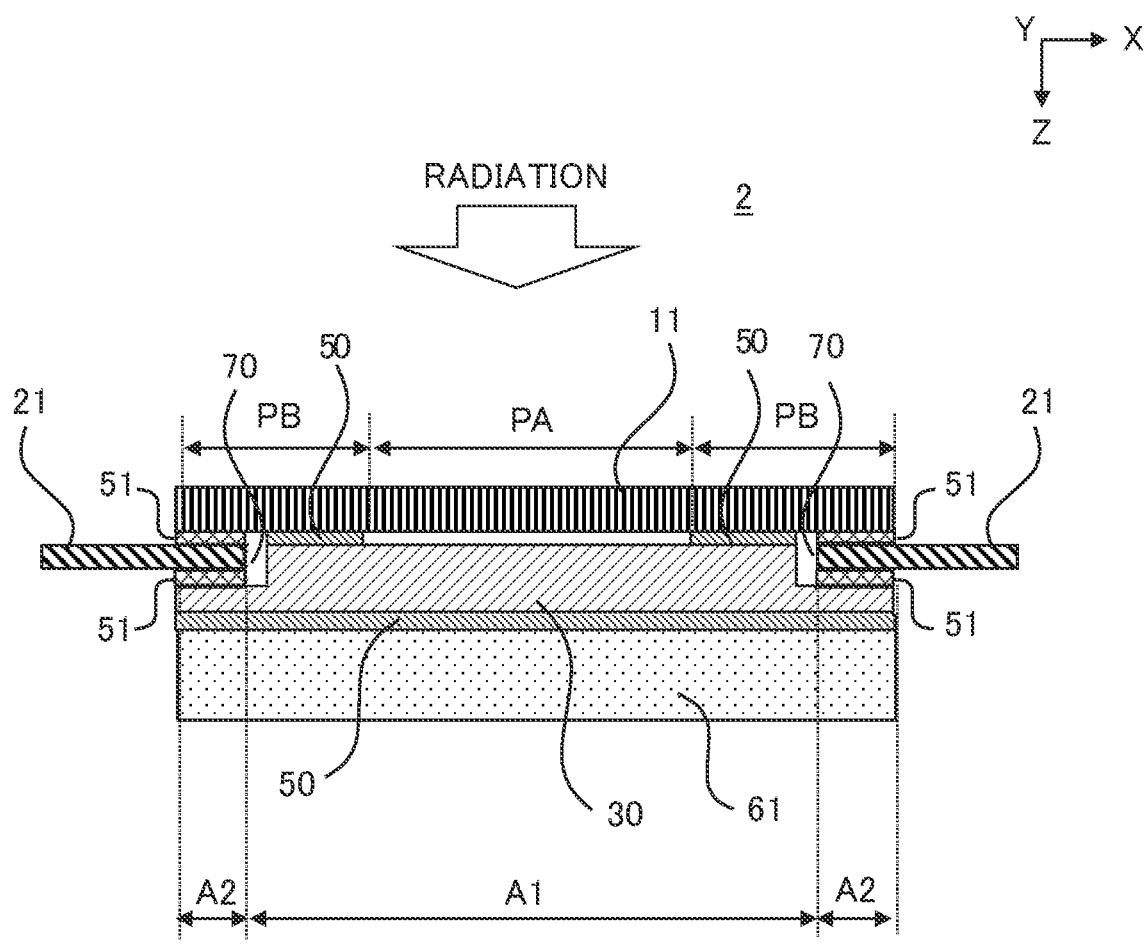
FIG. 3 is a cross-sectional view of a radiation detector 2 according to Embodiment 2.
Figure 4:
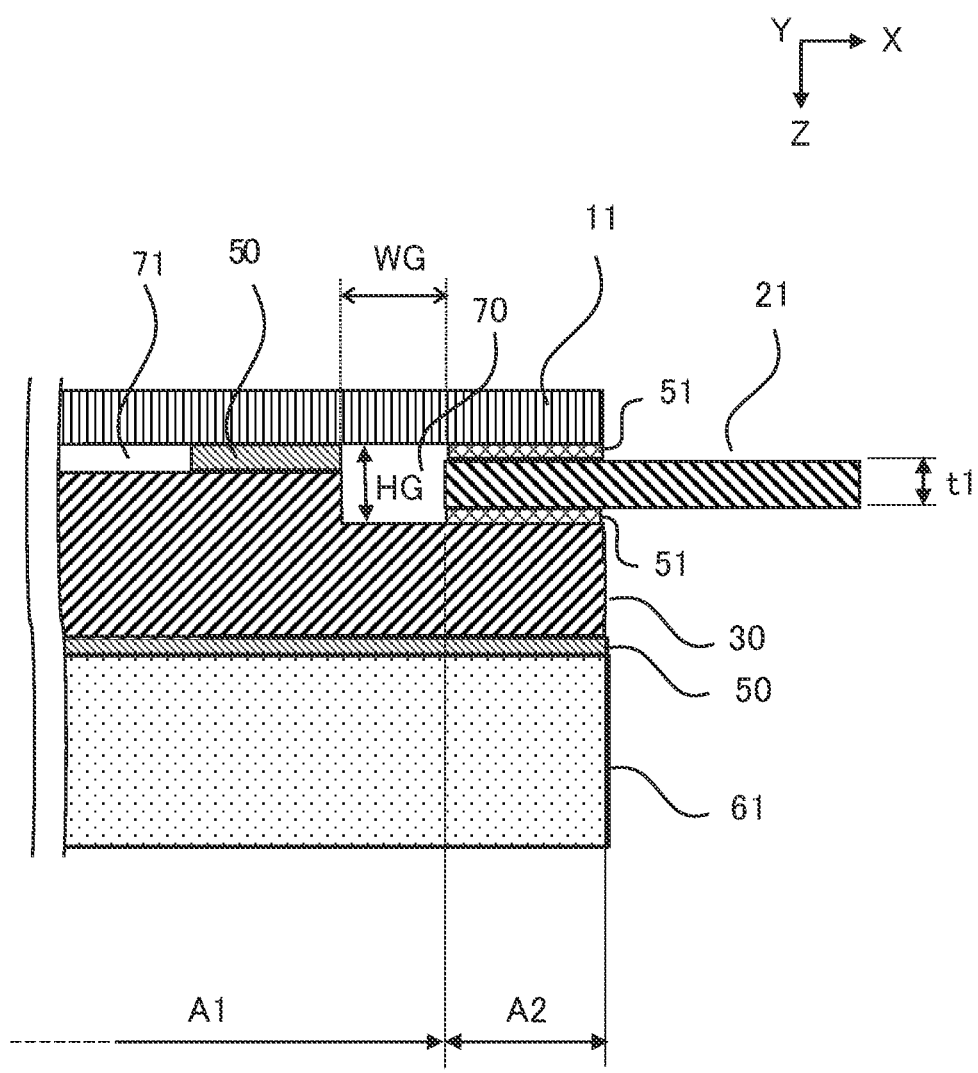
FIG. 4 is a partially enlarged view of a right side part of FIG. 3.

A radiation detector 2 according to Embodiment 2 is described with reference to FIGS. 3 and 4. Also in the radiation detector 2 of the present embodiment, the appearance in plan view as viewed from the direction in which the radiation is incident is similar to that in FIG. 1B. FIG. 3 illustrates a cross section taken along line C-C of FIG. 1B, and FIG. 4 illustrates a partially enlarged view of a right side part of FIG. 3. Elements common to the radiation detector 1 according to Embodiment 1 are denoted by the same reference numerals, and the description thereof is simplified or omitted.

Similarly to Embodiment 1, in the present embodiment, in the semiconductor layer 11, assuming that a main surface on the radiation incident side is referred to as a front surface, and a main surface on the opposite side is referred to as a back surface, a first area A1 including a detection area PA and a part of a peripheral area PB on the back surface faces the heat conduction member 30. A second area A2 including the remaining part of the peripheral area PB on the back surface faces the circuit board 21.

In Embodiment 1, the back surface of the semiconductor layer 11 and the heat conduction member 30 are bonded by the adhesive layer 51. Alternatively, in the present embodiment, the semiconductor layer 11 is connected to the heat conduction member 30 by the buffer member 50 in at least a part of the peripheral area PB. In this part, the back surface of the semiconductor layer 11 and the buffer member 50 are in contact with each other, and the buffer member 50 and the heat conduction member 30 are in contact with each other.

The buffer member 50 has a function as a buffer material for preventing an excessive force from being applied to the thin semiconductor layer 11 having weak mechanical strength due to the application of an external force when the radiation detector 2 is installed in the device or the imbalance of thermal contraction of each part at the time of cooling. In addition, the buffer member 50 has a function as a heat conduction path connecting the semiconductor layer 11 and the heat conduction member 30. The buffer member 50 is preferably configured with a pseudoplastic fluid or an elastic body having a smaller elastic modulus than the adhesive layer 51. As the pseudoplastic fluid, for example, grease can be used. As the elastic body, an adhesive, a double-sided tape, a die attach film, or the like, which has an elastic modulus smaller than the elastic modulus of the adhesive layer 51, can be used. The area where the buffer member 50 is provided is not limited to the example illustrated in FIG. 3, and for example, the buffer member 50 may be provided on the entire surface of the first area A1 excluding a part corresponding to the space 70.

When a member that can be easily deformed by an external force such as an adhesive, a double-sided tape, or a die attach film, which has an elastic modulus smaller than that of the adhesive layer 51 is used as the buffer member, the elastic modulus of the buffer member is desirably 1/10 or less of the elastic modulus of the adhesive layer 51. For example, if the elastic modulus of the adhesive layer 51 is within a range of 150 to 8,000 MPa, the elastic modulus of the buffer member is desirably 0.1 MPa or more and 1/10 or less of the elastic modulus of the adhesive layer 51.

In the present embodiment, a pseudoplastic fluid is suitably used as the buffer member. The pseudoplastic fluid is a fluid in which the viscosity decreases when a force is applied, that is, the viscosity coefficient decreases as the velocity gradient increases. The pseudoplastic fluid has a property in which the stronger the stress is, the more easily the pseudoplastic fluid flows, unlike Bingham fluids and dilatant fluids. In the present embodiment, grease which is a pseudoplastic fluid and is a semi-solid or semi-fluid lubricant can be suitably used as the buffer member. Specifically, for example, grease that has a worked penetration of 200 to 385, which indicates the hardness of the grease, is slightly hard to soft, but is not a fluid at normal temperature is used. In order to suppress evaporation to contaminate the surroundings, grease having an evaporation amount of 1 wt % or less per 24 hours at 200° C. is suitable. Specifically, HIVAC-G or KS-660B manufactured by Shin-Etsu Chemical Co., Ltd. can be used. For example, grease obtained by mixing fine particles of a high thermal conductive material such as silver may be used.

Assuming that the circuit board 21 and the heat conduction member 30 are assembled in a state of being in contact with each other in an X direction, if the linear expansion coefficient of the circuit board 21 is larger than the linear expansion coefficient of the heat conduction member 30, a disadvantage occurs when the circuit board 21 is cooled. That is, the circuit board 21 tends to contract more than the heat conduction member 30 contracts along a main surface direction due to the difference in the linear expansion coefficient but cannot contract in the main surface direction if the circuit board 21 is in contact with the heat conduction member 30 so as to surround the heat conduction member 30. Therefore, warpage or distortion occurs in the circuit board 21. If warpage or distortion occurs in the circuit board 21, a force is applied to the semiconductor layer 11 in contact with the upper surface of the circuit board 21. Even if the force applied to the semiconductor layer 11 is reduced by the effect of the buffer member 50, when the thickness of the semiconductor layer 11 is small, the semiconductor layer 11 may be damaged.

On the other hand, according to the present embodiment, the space 70 is provided between the circuit board 21 and the heat conduction member 30, and a height HG of the space 70 is larger than a thickness t1 of the circuit board 21 in a direction perpendicular to the main surface of the semiconductor layer 11 (Z direction), as illustrated in FIG. 4. In other words, when the radiation detector 2 is seen through from the direction perpendicular to the main surface of the semiconductor layer 11 (Z direction), the first area A1 in which the semiconductor layer 11 and the heat conduction member 30 overlap in this order, and the circuit board 21 does not overlap, and the second area A2 in which the semiconductor layer 11, the circuit board 21, and the heat conduction member 30 overlap in this order are provided adjacent to each other. In the first area A1, the space 70 that separates the semiconductor layer 11 and the heat conduction member 30 is provided at a boundary portion with the second area A2, and the height HG of the space 70 in the direction perpendicular to the main surface of the semiconductor layer 11 (Z direction) is larger than the thickness t1 of the circuit board 21.

Also, in a direction parallel to the main surface of the semiconductor layer 11 (X direction), a width WG of the space 70 is set to 20 μm or more in a state where the radiation detector 2 is placed at normal temperature. For this reason, even if the linear expansion coefficient of the circuit board 21 is larger than the linear expansion coefficient of the heat conduction member 30, the circuit board 21 that tends to contract in the main surface direction when cooled below the normal temperature is not in contact with the heat conduction member 30, or the force applied therebetween can be reduced. The occurrence of warpage or distortion in the circuit board 21 can also be reduced. Therefore, the semiconductor layer 11 having a small thickness is prevented from being damaged. Note that, although the XZ cross section is illustrated in FIG. 3, it is desirable to similarly provide the space 70 also in the YZ cross section. The space 70 may have a part provided along the X direction and a part provided along the Y direction. Furthermore, a frame-shaped or annular space 70 surrounding the outer side of the detection area PA in plan view may be provided.

In the present embodiment, since the width WG of the space 70 is set to 20 μm or more in consideration of the deviation from the set temperature at the time of cooling, the shape accuracy of the member, and the like, a sufficient clearance is secured between the circuit board 21 and the heat conduction member 30. In addition, since the buffer member 50 is provided, an excessive force can be effectively prevented from being applied to the thin semiconductor layer 11 having weak mechanical strength due to the application of an external force when the radiation detector 2 is installed in the device or the imbalance of thermal contraction of each part at the time of cooling. That is, it is possible to realize the radiation detector 2 that can obtain a radiation image with high image quality without being damaged even if the semiconductor element is cooled during use. In order to prevent the radiation from colliding with air and scattering, the radiation detector 2 may be operated in vacuum or under low atmospheric pressure.

Embodiment 3

Figure 5:
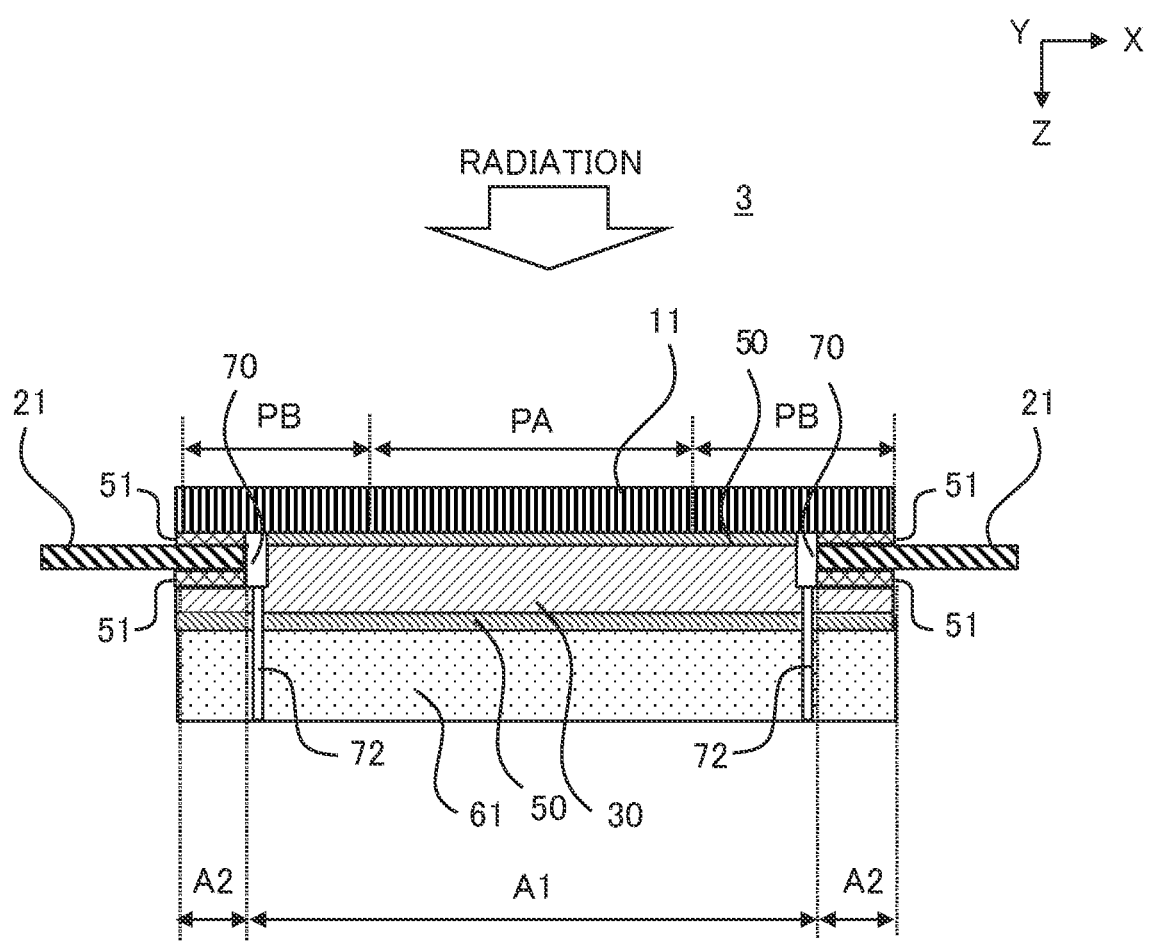
FIG. 5 is a cross-sectional view of a radiation detector 3 according to Embodiment 3.
Figure 6:
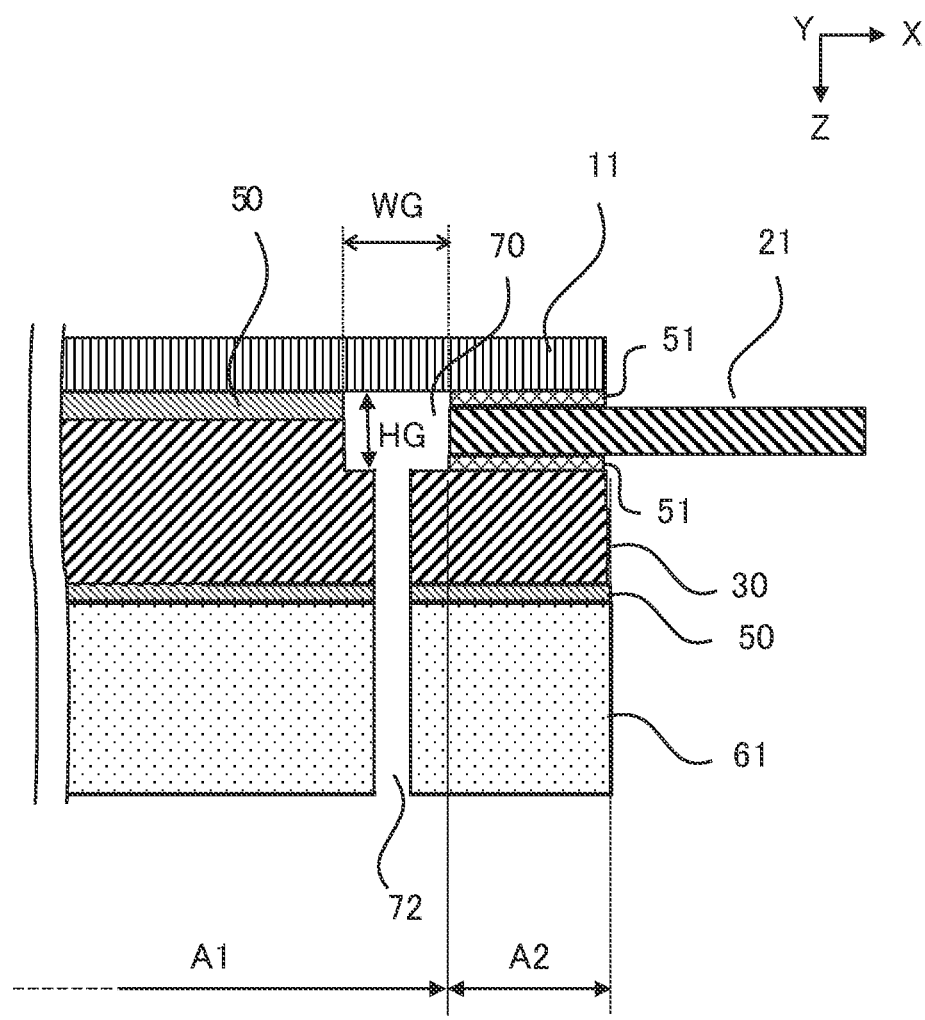
FIG. 6 is a partially enlarged view of a right side part of FIG. 5.

A radiation detector 3 according to Embodiment 3 is described with reference to FIGS. 5 and 6. Also in the radiation detector 3 of the present embodiment, the appearance in plan view as viewed from the direction in which the radiation is incident is similar to that in FIG. 1B. FIG. 5 illustrates a cross section taken along line C-C of FIG. 1B, and FIG. 6 illustrates a partially enlarged view of a right side part of FIG. 5. Elements common to the radiation detector 1 according to Embodiment 1 are denoted by the same reference numerals, and the description thereof is simplified or omitted.

Similarly to Embodiment 1, in the present embodiment, in the semiconductor layer 11, assuming that a main surface on the radiation incident side is referred to as a front surface, and a main surface on the opposite side is referred to as a back surface, a first area A1 including a detection area PA and a part of a peripheral area PB on the back surface faces the heat conduction member 30. A second area A2 including the remaining part of the peripheral area PB on the back surface faces the circuit board 21.

Also according to the present embodiment, the space 70 is provided between the circuit board 21 and the heat conduction member 30, and a height HG of the space 70 is larger than a thickness t1 of the circuit board 21 in a direction perpendicular to the main surface of the semiconductor layer 11 (Z direction), as illustrated in FIG. 6. In other words, when the radiation detector 3 is seen through from the direction perpendicular to the main surface of the semiconductor layer 11 (Z direction), the first area A1 in which the semiconductor layer 11 and the heat conduction member 30 overlap in this order, and the circuit board 21 does not overlap, and the second area A2 in which the semiconductor layer 11, the circuit board 21, and the heat conduction member 30 overlap in this order are provided adjacent to each other. In the first area A1, the space 70 that separates the semiconductor layer 11 and the heat conduction member 30 is provided at a boundary portion with the second area A2, and the height HG of the space 70 in the direction perpendicular to the main surface of the semiconductor layer 11 (Z direction) is larger than the thickness t1 of the circuit board 21. Also, in a direction parallel to the main surface of the semiconductor layer 11 (X direction), a width WG of the space 70 is set to 20 μm or more in a state where the radiation detector 3 is placed at normal temperature. Note that, although an XZ cross section is illustrated in FIG. 5, it is desirable to similarly provide the space 70 also in a YZ cross section. The space 70 may have a part provided along the X direction and a part provided along the Y direction. Furthermore, a frame-shaped or annular space 70 surrounding the outer side of the detection area PA in plan view may be provided.

In the present embodiment, a communication path 72 for allowing the space 70 and an external space to communicate with each other is provided. The communication path 72 may penetrate the heat conduction member 30, the buffer member 50, and the cooling device 61 to connect the space 70 and the external space as illustrated in the drawing or may be bent in the X direction, for example, in the heat conduction member 30 to connect the space 70 and the external space. In short, it is sufficient that the space 70 and the external space communicate with each other. Note that, although the XZ cross section is illustrated in FIG. 5, it is possible to similarly provide the communication path 72 also in the YZ cross section. The space 70 and the communication path 72 may be provided so as to surround the outside of the detection area PA in plan view, or the communication path 72 may be provided at any distance.

In a case where the space 70 is sealed, if an atmospheric pressure difference occurs between the space 70 and the external space, a force may be locally applied to the thin semiconductor layer 11 having weak mechanical strength. Particularly, if the radiation detector is a device that is operated in vacuum or under an environment of low atmospheric pressure in order to prevent the radiation from colliding with air and scattering, the possibility that the force may be locally applied to the semiconductor layer 11 increases. In this regard, even when the radiation detector 3 of the present embodiment including the communication path 72 is operated in an environment in which the atmospheric pressure in the external space is different from the atmospheric pressure, a pressure difference is not generated between the space 70 and the external space, and it is possible to prevent the force caused by the pressure difference from being applied to the semiconductor layer 11. A width of the communication path 72 in the X direction may be equal to the width WG of the space 70, the width of the communication path 72 may be larger than the width WG of the space 70, or the width of the communication path 72 may be smaller than the width WG of the space 70.

Of course, similarly to Embodiment 1, since the width WG of the space 70 is set to 20 μm or more in consideration of the deviation from the set temperature at the time of cooling, the shape accuracy of the member, and the like, a sufficient clearance is secured between the circuit board 21 and the heat conduction member 30. Therefore, an excessive force can be effectively prevented from being applied to the thin semiconductor layer 11 having weak mechanical strength due to the imbalance of thermal contraction of each part at the time of cooling. That is, it is possible to realize the radiation detector 3 that can obtain a radiation image with high image quality without being damaged even if the semiconductor element is cooled during use.

Embodiment 4

Figure 9A:
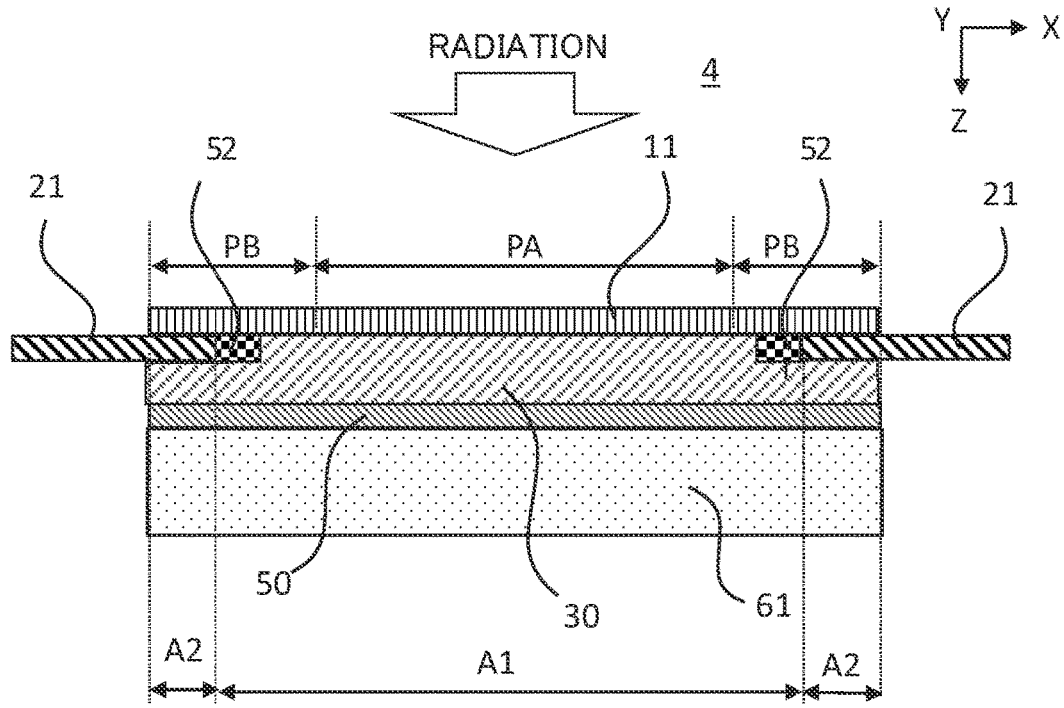
FIG. 9A is a cross-sectional view of a radiation detector 4 according to Embodiment 4.
Figure 9B:
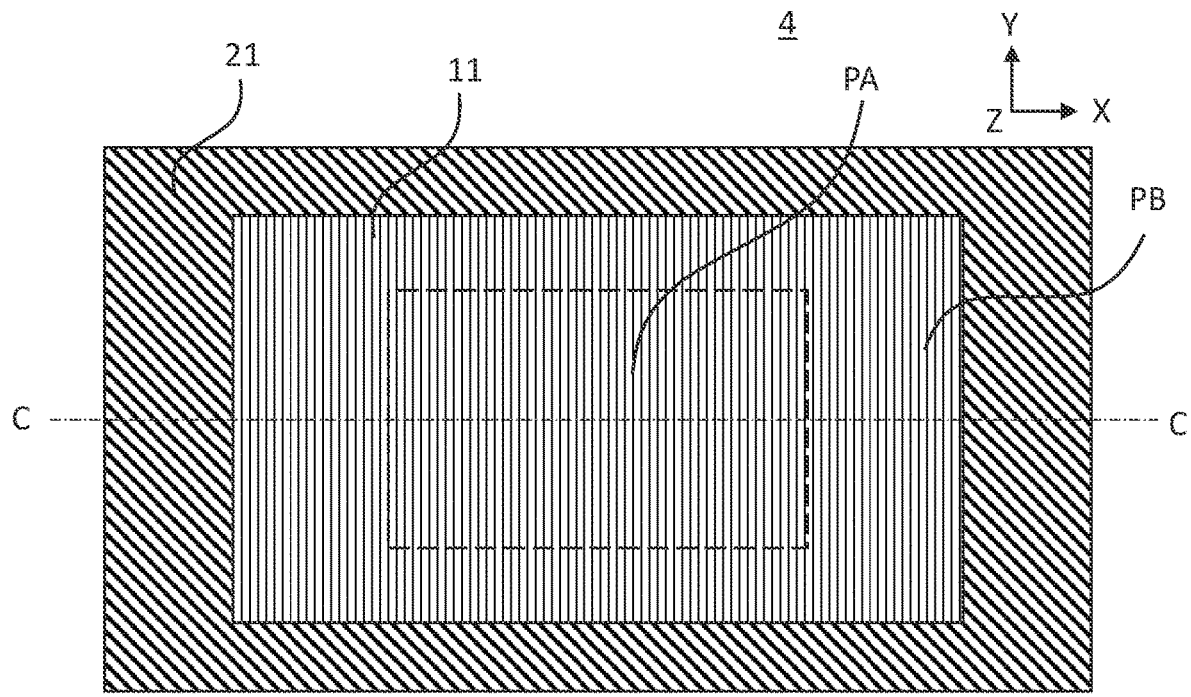
FIG. 9B is a plan view of the radiation detector 4 according to Embodiment 4.
Figure 10:
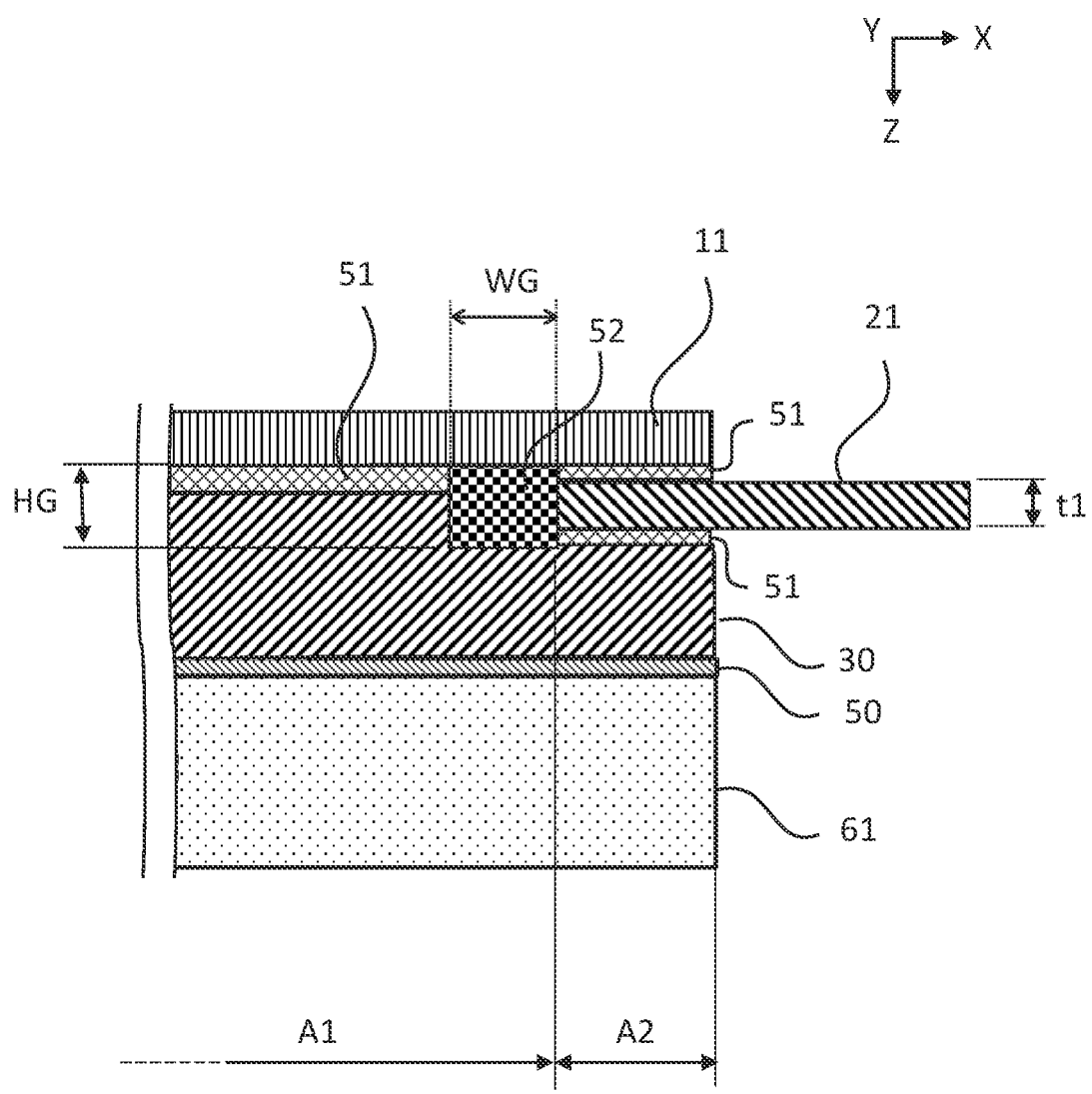
FIG. 10 is a partially enlarged view of a right side part of FIG. 9A.

A radiation detector 4 according to Embodiment 4 is described with reference to FIGS. 9A, 9B and 10. As shown in FIG. 9B, also in the radiation detector 4 of the present embodiment, the appearance in plan view as viewed from the direction in which the radiation is incident is similar to that in FIG. 1B. FIG. 9A illustrates a cross section taken along line C-C of FIG. 9B, and FIG. 10 illustrates a partially enlarged view of a right side part of FIG. 9A. Elements common to the radiation detector 1 according to Embodiment 1 are denoted by the same reference numerals, and the description thereof is simplified or omitted.

Similarly to Embodiment 1, in the present embodiment, in the semiconductor layer 11, assuming that a main surface on the radiation incident side is referred to as a front surface, and a main surface on the opposite side is referred to as a back surface, a first area A1 including a detection area PA and a part of a peripheral area PB on the back surface faces the heat conduction member 30. A second area A2 including the remaining part of the peripheral area PB on the back surface faces the circuit board 21.

In Embodiment 1, the space 70 that separates the semiconductor layer 11 and the heat conduction member 30 is provided between the semiconductor layer 11 and the heat conduction member 30. Alternatively, in the present embodiment, a buffer member 52 is disposed at a location corresponding to the space 70 in Embodiment 1. As illustrated in FIG. 10, the buffer member 52 is in contact with all or at least one of the back surface of the semiconductor layer 11, the adhesive layer 51, the circuit board 21, and the heat conduction member 30.

The buffer member 52 has a function as a buffer material for preventing an excessive force from being applied to the thin semiconductor layer 11 having weak mechanical strength due to the application of an external force when the radiation detector 4 is installed in the device or the imbalance of thermal contraction of each part at the time of cooling. In addition, the buffer member 50 has a function as a heat conduction path connecting the semiconductor layer 11 and the heat conduction member 30. The buffer member 52 is a pseudoplastic fluid or an elastic body. As the pseudoplastic fluid, for example, grease can be used. As the elastic body, an elastic material having a smaller elastic modulus than the semiconductor layer 11, the adhesive layer 51, the circuit board 21, and the heat conduction member 30 that are in contact with the buffer member 52 is used, and for example, a resin or the like can be used. The elastic modulus of the buffer member is desirably, for example, 1/10 or less of the smallest elastic modulus of the elastic moduli of the semiconductor layer 11, the adhesive layer 51, the circuit board 21, and the heat conduction member 30.

Assuming that the circuit board 21 and the heat conduction member 30 are assembled in a state of being in contact with each other in an X direction, if the linear expansion coefficient of the circuit board 21 is larger than the linear expansion coefficient of the heat conduction member 30, a disadvantage occurs when the circuit board 21 is cooled. That is, the circuit board 21 tends to contract more than the heat conduction member 30 contracts along a main surface direction due to the difference in the linear expansion coefficient but cannot contract in the main surface direction if the circuit board 21 is in contact with the heat conduction member 30 so as to surround the heat conduction member 30. Therefore, warpage or distortion occurs in the circuit board 21. If warpage or distortion occurs in the circuit board 21, a force is applied to the semiconductor layer 11 in contact with the upper surface of the circuit board 21. Even if the force applied to the semiconductor layer 11 is reduced by the effect of the buffer member 50 that is provided under the heat conduction member 30, when the thickness of the semiconductor layer 11 is small, the semiconductor layer 11 may be damaged.

On the other hand, according to the present embodiment, the buffer member 52 is provided between the circuit board 21 and the heat conduction member 30, and a height HG of the buffer member 52 is larger than a thickness t1 of the circuit board 21 in a direction perpendicular to the main surface of the semiconductor layer 11 (Z direction), as illustrated in FIG. 10. In other words, when the radiation detector 4 is seen through from the direction perpendicular to the main surface of the semiconductor layer 11 (Z direction), the first area A1 in which the semiconductor layer 11 and the heat conduction member 30 overlap in this order, and the circuit board 21 does not overlap, and the second area A2 in which the semiconductor layer 11, the circuit board 21, and the heat conduction member 30 overlap in this order are provided adjacent to each other. In the first area A1, the buffer member 52 that separates the semiconductor layer 11 and the heat conduction member 30 is provided at a boundary portion with the second area A2, and the height HG of the buffer member 52 in the direction perpendicular to the main surface of the semiconductor layer 11 (Z direction) is larger than the thickness t1 of the circuit board 21.

Also, in a direction parallel to the main surface of the semiconductor layer 11 (X direction), a width WG of the buffer member 52 is set to 20 μm or more in a state where the radiation detector 4 is placed at normal temperature. For this reason, even if the linear expansion coefficient of the circuit board 21 is larger than the linear expansion coefficient of the heat conduction member 30, the circuit board 21 that tends to contract in the main surface direction when cooled below the normal temperature is not in contact with the heat conduction member 30, or the force applied therebetween can be reduced. The occurrence of warpage or distortion in the circuit board 21 can also be reduced. Therefore, the semiconductor layer 11 having a small thickness is prevented from being damaged. Note that, although the XZ cross section is illustrated in FIG. 9A, it is desirable to similarly provide the buffer member 52 also in the YZ cross section. The buffer member 52 may have a part provided along the X direction and a part provided along the Y direction. Furthermore, a frame-shaped or annular buffer member 52 surrounding the outer side of the detection area PA in plan view may be provided.

In the present embodiment, since the width WG of the buffer member 52 is set to 20 μm or more in consideration of the deviation from the set temperature at the time of cooling, the shape accuracy of the member, and the like, a sufficient distance is secured between the circuit board 21 and the heat conduction member 30. In addition, since the buffer member 52 is provided, an excessive force can be effectively prevented from being applied to the thin semiconductor layer 11 having weak mechanical strength due to the application of an external force when the radiation detector 4 is installed in the device or the imbalance of thermal contraction of each part at the time of cooling. That is, it is possible to realize the radiation detector 4 that can obtain a radiation image with high image quality without being damaged even if the semiconductor element is cooled during use.

In order to prevent the radiation from colliding with the air and scattering, when the radiation detector is operated in vacuum or under low atmospheric pressure, in Embodiment 1, a force may be applied to the semiconductor layer 11 due to a pressure difference between the gas confined in the space 70 and the operating environment. Alternatively, in the present embodiment, since the buffer member 52 is provided, the space 70 substantially does not exist or has a small volume. Therefore, according to the present embodiment, in the case of being operated under an environment different from the atmospheric pressure, the force applied to the semiconductor layer 11 is reduced due to the pressure difference as compared with Embodiment 1, and higher safety is secured.

Embodiment 5

Figure 11:
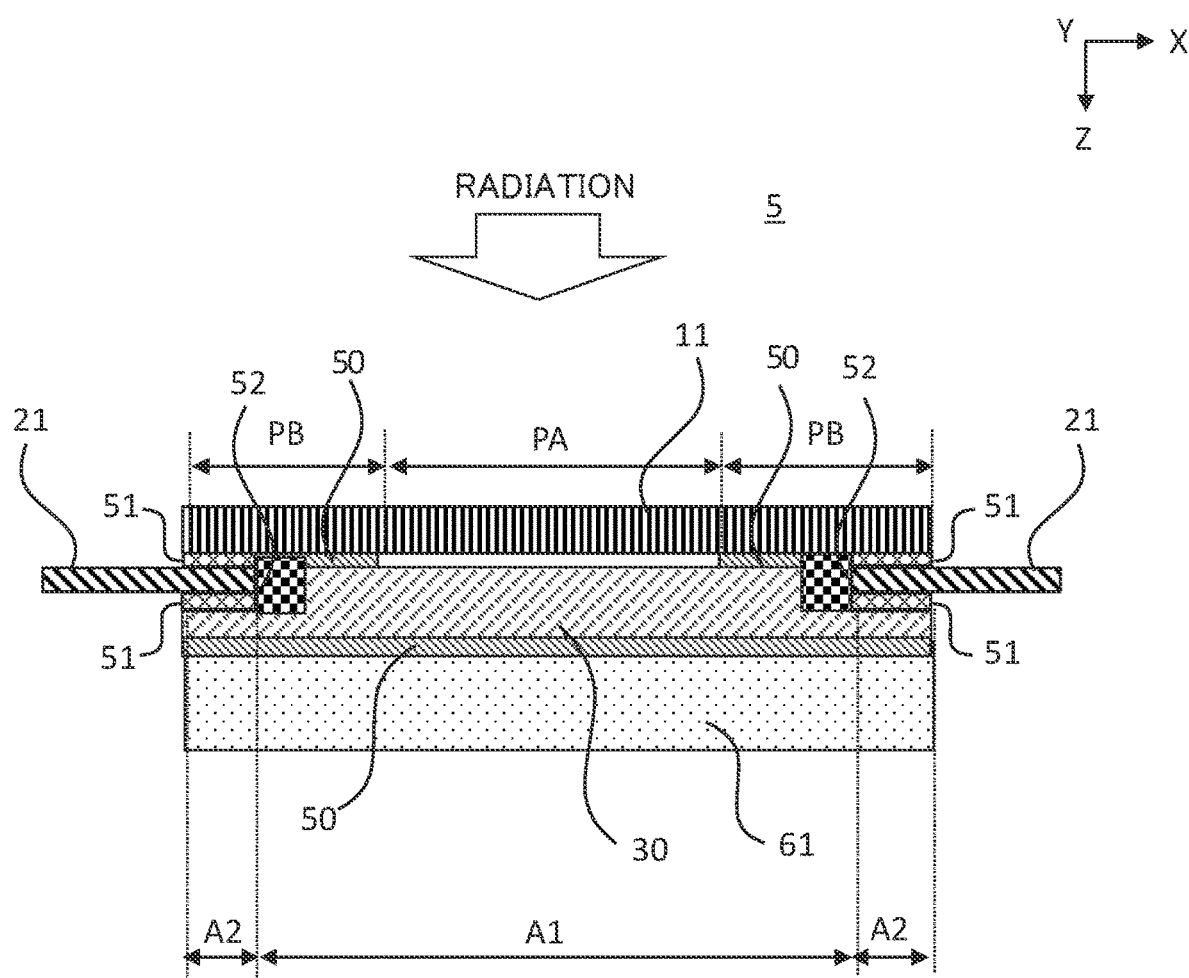
FIG. 11 is a cross-sectional view of a radiation detector 5 according to Embodiment 5.
Figure 12:
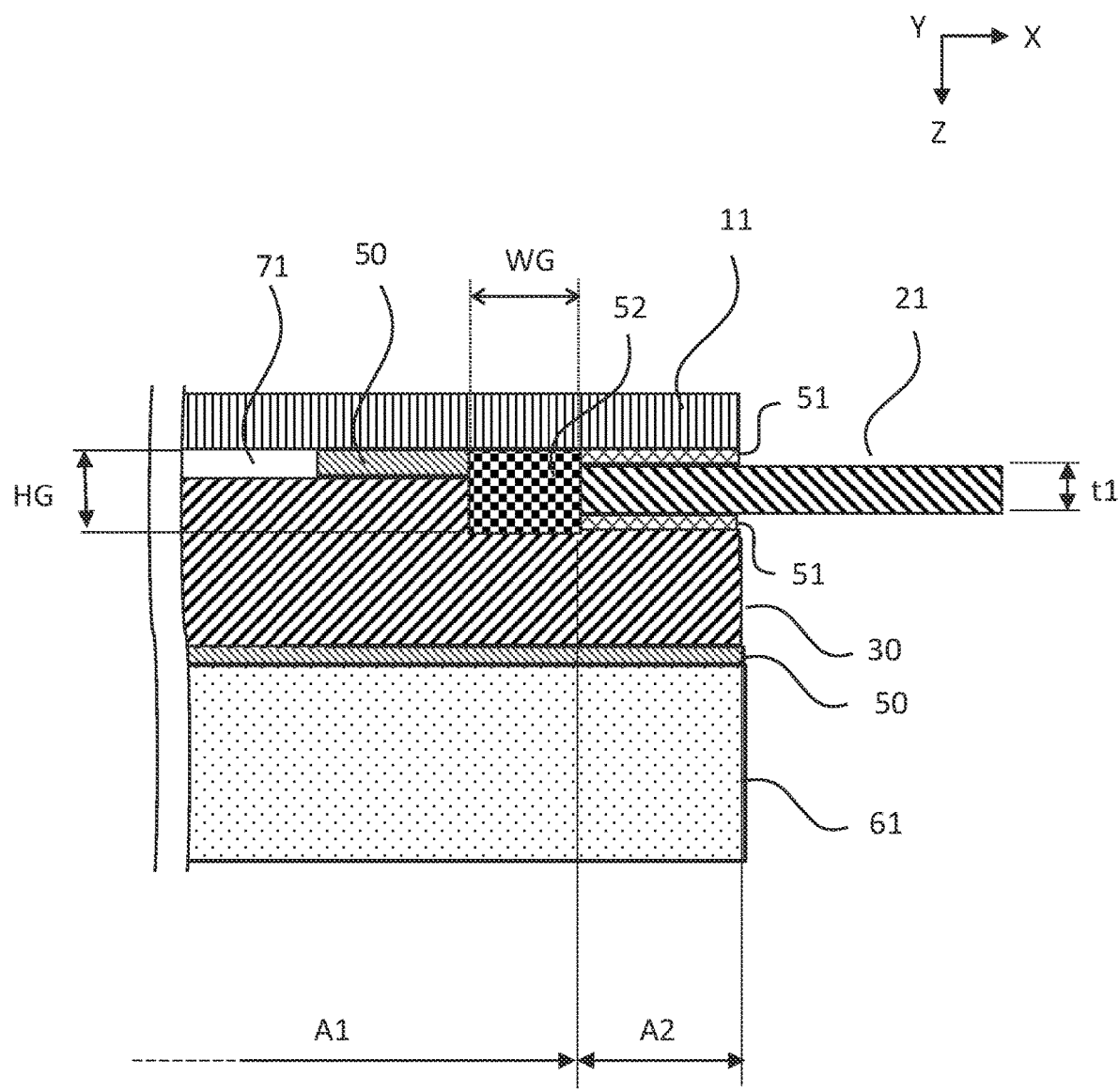
FIG. 12 is a partially enlarged view of a right side part of FIG. 11.

A radiation detector 5 according to Embodiment 5 is described with reference to FIGS. 11 and 12. Also in the radiation detector 5 of the present embodiment, the appearance in plan view as viewed from the direction in which the radiation is incident is similar to that in FIG. 1B. FIG. 11 illustrates a cross section taken along line C-C of FIG. 1B, and FIG. 12 illustrates a partially enlarged view of a right side part of FIG. 11. Elements common to the radiation detector 1 according to Embodiment 1 or the radiation detector 2 according to Embodiment 2 are denoted by the same reference numerals, and the description thereof is simplified or omitted.

As illustrated in FIG. 12, similarly to Embodiment 2, in the present embodiment, in the semiconductor layer 11, assuming that a main surface on the radiation incident side is referred to as a front surface, and a main surface on the opposite side is referred to as a back surface, a first area A1 including a detection area PA and a part of a peripheral area PB on the back surface faces the heat conduction member 30. A second area A2 including the remaining part of the peripheral area PB on the back surface faces the circuit board 21.

In Embodiment 2, the space 70 that separates the semiconductor layer 11 and the heat conduction member 30 is provided between the semiconductor layer 11 and the heat conduction member 30. Alternatively, in the present embodiment, the buffer member 52 is disposed at a location corresponding to the space 70 in Embodiment 2. As illustrated in FIG. 11, the buffer member 52 is in contact with all or at least one of the back surface of the semiconductor layer 11, the adhesive layer 51, the circuit board 21, and the heat conduction member 30.

The buffer member 52 in the present embodiment is made of the same material as the buffer member 52 used in Embodiment 4, is arranged in the same manner, and has the same effect.

Embodiment 6

Figure 13:
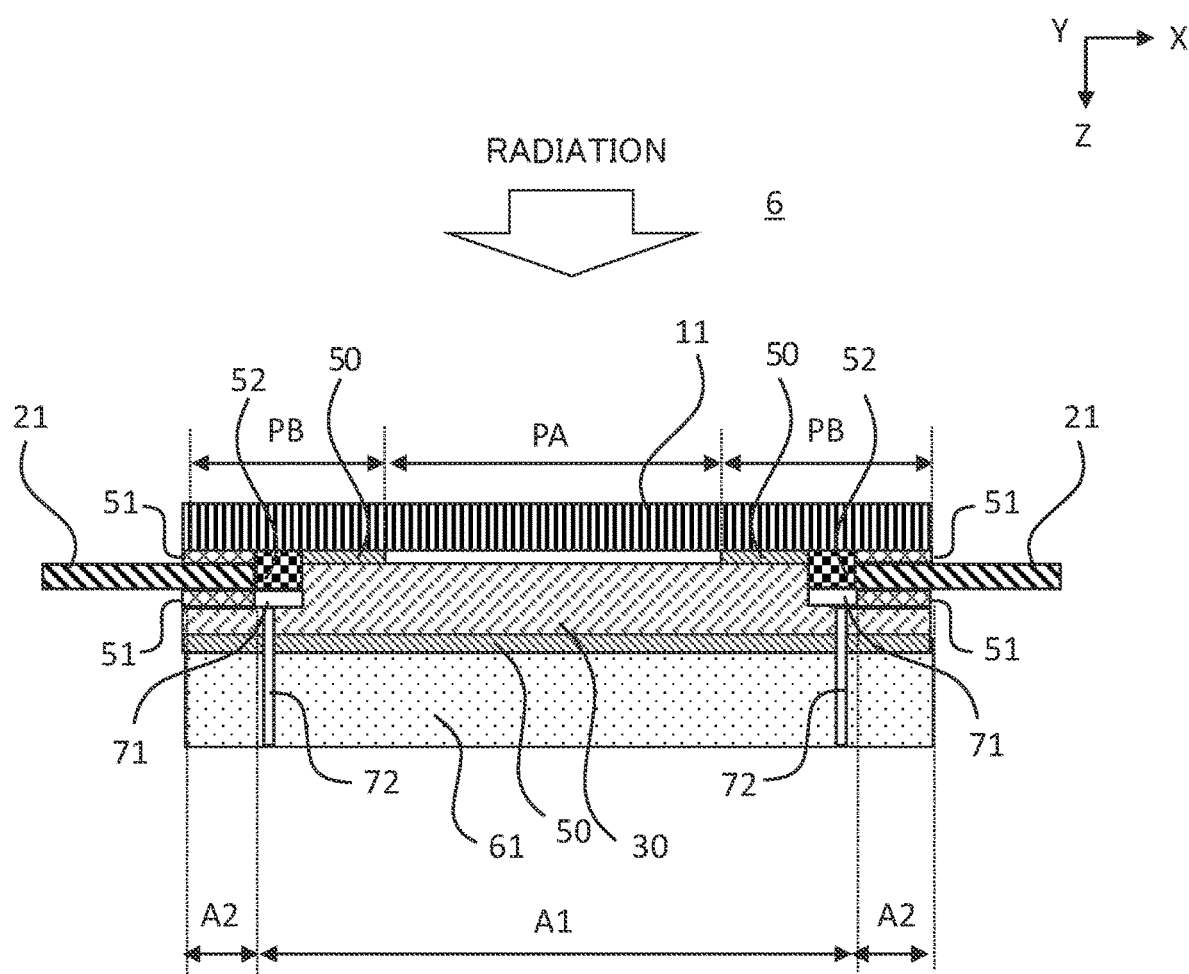
FIG. 13 is a cross-sectional view of a radiation detector 6 according to Embodiment 6.
Figure 14:
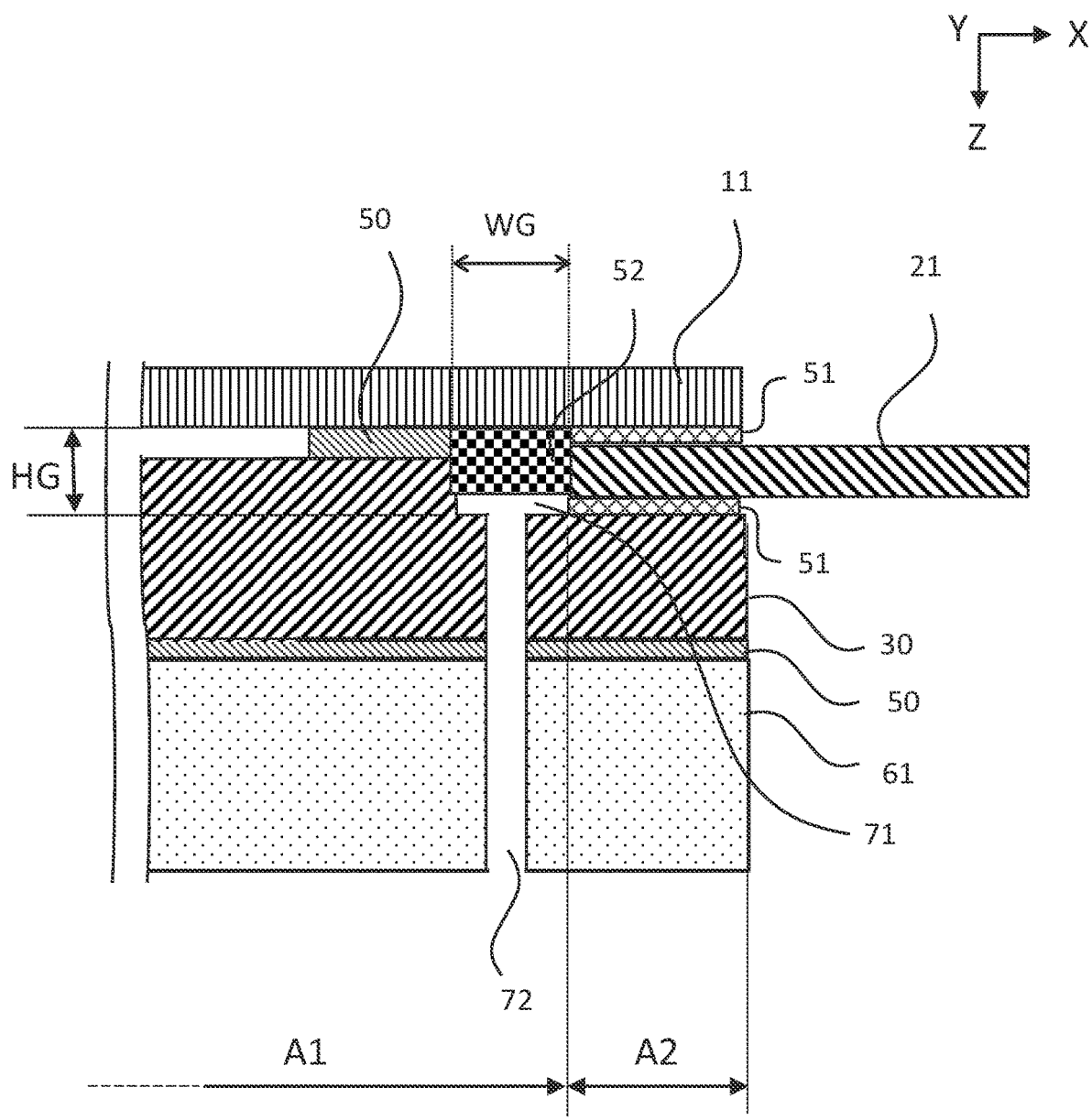
FIG. 14 is a partially enlarged view of a right side part of FIG. 13.

A radiation detector 6 according to Embodiment 6 is described with reference to FIGS. 13 and 14. Also in the radiation detector 6 of the present embodiment, the appearance in plan view as viewed from the direction in which the radiation is incident is similar to that in FIG. 1B. FIG. 13 illustrates a cross section taken along line C-C of FIG. 1B, and FIG. 14 illustrates a partially enlarged view of a right side part of FIG. 13. Elements common to the radiation detector 1 according to Embodiment 1 and the radiation detector 3 according to Embodiment 3 are denoted by the same reference numerals, and the description thereof is simplified or omitted.

Similarly to Embodiment 3, in the present embodiment, in the semiconductor layer 11, assuming that a main surface on the radiation incident side is referred to as a front surface, and a main surface on the opposite side is referred to as a back surface, a first area A1 including a detection area PA and a part of a peripheral area PB on the back surface faces the heat conduction member 30. A second area A2 including the remaining part of the peripheral area PB on the back surface faces the circuit board 21.

In Embodiment 3, the space 70 that separates the semiconductor layer 11 and the heat conduction member 30 is provided between the semiconductor layer 11 and the heat conduction member 30. Alternatively, in the present embodiment, the buffer member 52 is disposed at a part of a location corresponding to the space 70 of Embodiment 3. As illustrated in FIG. 14, the buffer member 52 is in contact with all or at least one of the back surface of the semiconductor layer 11, the adhesive layer 51, the circuit board 21, and the heat conduction member 30. In the example of FIG. 14, a space 71 is interposed between the buffer member 52 and the heat conduction member 30 on the side of the cooling device 61 with respect to the buffer member 52, but the space 71 may be interposed between the buffer member 52 and another member. All or a part of the space 71 is connected to the communication path 72.

The buffer member 52 in the present embodiment is made of the same material as the buffer member 52 used in Embodiments 4 and 5, is arranged in the same manner, and has the same effect.

In order to prevent the radiation from colliding with the air and scattering, when the radiation detector is operated in vacuum or under low atmospheric pressure, in Embodiment 1, a force may be applied to the semiconductor layer 11 due to a pressure difference between the gas confined in the space 70 and the operating environment. Alternatively, in the present embodiment, all or a part of the space 71 is connected to the communication path 72. Therefore, even when the radiation detector 6 of the present embodiment is operated in an environment in which the atmospheric pressure in the external space is different from the atmospheric pressure, a pressure difference is not generated between the space 71 and the external space, and it is possible to prevent the force caused by the pressure difference from being applied to the semiconductor layer 11.

Embodiment 7

Figure 7:
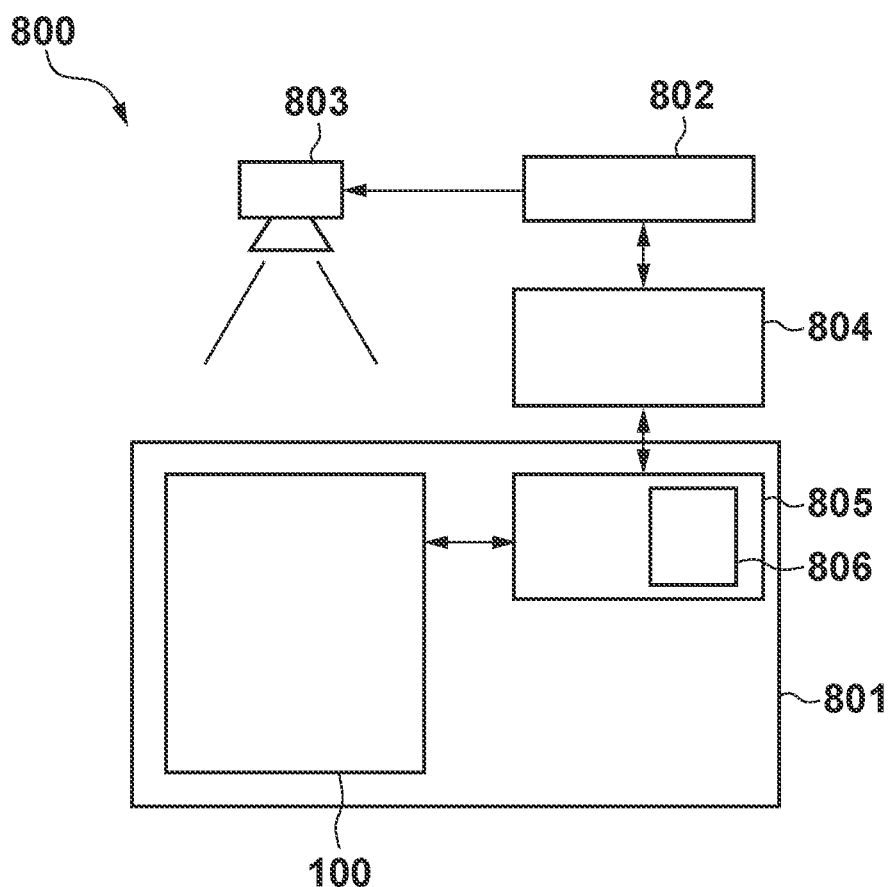
FIG. 7 is a schematic diagram illustrating a radiation image capturing system according to Embodiment 7.

With reference to FIG. 7, a radiation image capturing device 801 in which the radiation detector according to any one of Embodiments 1 to 6 described above is incorporated and a radiation image capturing system 800 using the corresponding radiation image capturing device are described.

The radiation image capturing system 800 is configured to electrically capture an optical image formed by radiation to obtain an electrical radiation image (that is, radiation image data). The radiation image capturing system 800 includes, for example, the radiation image capturing device 801, an exposure control unit 802, a radiation source 803, and a computer 804. The radiation image capturing system 800 can display a captured radiation image on a display device (not illustrated) or transmit the radiation image data to the outside via a communication device (not illustrated). The radiation image capturing system 800 can be suitably used in fields such as medical image diagnosis and non-destructive inspection.

The radiation source 803 for irradiation with radiation starts radiation emission in accordance with an exposure command from the exposure control unit 802. The radiation emitted from the radiation source 803 is applied to the radiation image capturing device 801 through a subject (not illustrated). The radiation source 803 stops the radiation emission in accordance with a stop command from the exposure control unit 802.

The radiation image capturing device 801 includes a radiation detector 100 according to any one of Embodiments 1 to 6 described above, a control unit 805 for controlling the radiation detector 100, and a signal processing unit 806 for processing a signal output from the radiation detector 100.

For example, if a signal output from the radiation detector 100 is an analog signal, the signal processing unit 806 can perform A/D conversion on the analog signal and output the converted signal to the computer 804 as the radiation image data. Furthermore, the signal processing unit 806 may generate a stop signal for stopping radiation emission from the radiation source 803, for example, based on the signal output from the radiation detector 100. The stop signal is supplied to the exposure control unit 802 via the computer 804, and the exposure control unit 802 sends the stop command to the radiation source 803 in response to the stop signal.

The control unit 805 can be configured by, for example, a programmable logic device (PLD) such as a field programmable gate array (FPGA), an application specific integrated circuit (ASIC), a general-purpose computer into which a program is incorporated, or a combination of all or part thereof.

Furthermore, although the signal processing unit 806 is illustrated as being disposed in the control unit 805 or being a part of the function of the control unit 805, the present embodiment is not limited thereto. The control unit 805 and the signal processing unit 806 may be configured separately. Furthermore, the signal processing unit 806 may be disposed separately from the radiation image capturing device 801. For example, the computer 804 may have the function of the signal processing unit 806. Therefore, the signal processing unit 806 can be included in the radiation image capturing system 800 as a signal processing device that processes a signal output from the radiation image capturing device 801.

The computer 804 can perform processing for controlling the radiation image capturing device 801 and the exposure control unit 802, receiving radiation image data from the radiation image capturing device 801, and displaying the radiation image data as a radiation image. In addition, the computer 804 can function as an input unit for a user to input conditions for capturing a radiation image.

As an example of the sequence, in a case the exposure control unit 802 includes an exposure switch, when the exposure switch is turned on by the user, the exposure control unit sends an exposure command to the radiation source 803 and also sends a start notification indicating the start of radiation emission to the computer 804. The computer 804 that receives the start notification notifies the control unit 805 of the radiation image capturing device 801 of the start of the irradiation emission in response to the start notification. In response to this, the control unit 805 causes the radiation detector 100 to generate a signal corresponding to the incident radiation.

In the radiation image capturing device of the present embodiment and the radiation image capturing system using the radiation image capturing device, even if the radiation detector is cooled at the time of image capturing, it is possible to effectively prevent application of an excessive force to the thin semiconductor layer having weak mechanical strength due to the imbalance of thermal contraction of each part. For this reason, it is possible to realize a radiation image capturing device that is excellent in reliability and durability and can obtain a high-quality radiation image and to practically use the radiation image capturing device in various fields including medical use and industrial use.

Embodiment 8

Figure 8:
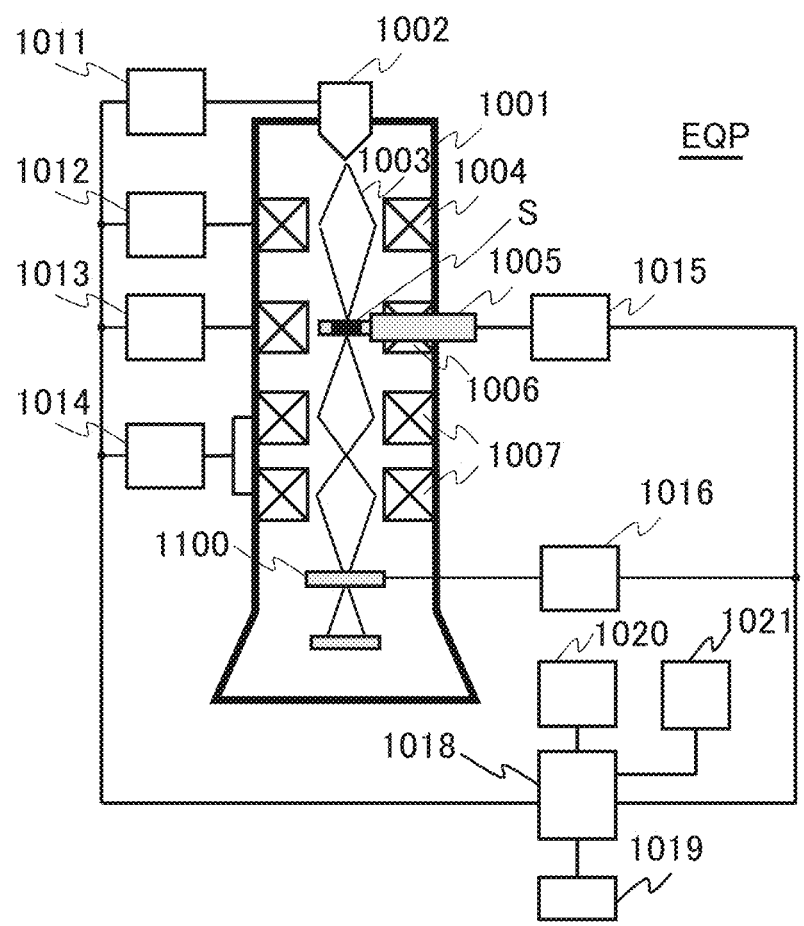
FIG. 8 is a schematic diagram illustrating a radiation image capturing system according to Embodiment 8.

As a radiation image capturing system into which the radiation detector according to any one of Embodiments 1 to 6 is incorporated, a transmission electron microscope (TEM) system is described with reference to a schematic configuration diagram of FIG. 8. An equipment EQP as the transmission electron microscope includes an electron beam source 1002 (electron gun), an irradiation lens 1004, a vacuum chamber 1001 (lens barrel), an objective lens 1006, a magnifying lens system 1007, and a radiation detector 1100.

An electron beam 1003, which is radiation emitted from the electron beam source 1002 (electron gun) as a radiation source, is focused by the irradiation lens 1004 and is applied to a sample S as an analysis target held in a sample holder. A space through which the electron beam 1003 passes is defined by the vacuum chamber 1001 (lens barrel) included in the equipment EQP, and this space is maintained in vacuum. Since the radiation detector 1100 is used in a vacuum, particularly Embodiments 3 and 6 can be suitably employed among Embodiments 1 to 6 described above.

The electron beam 1003 transmitted through the sample S is magnified by the objective lens 1006 and the magnifying lens system 1007 and forms an image on a light receiving surface of the radiation detector 1100. An electron optical system for irradiating the sample S with an electron beam is referred to as an irradiation optical system, and an electron optical system for causing the electron beam transmitted through the sample S to form an image on the light receiving surface of the radiation detector 1100 is referred to as an image forming optical system.

The electron beam source 1002 is controlled by an electron beam source control device 1011. The irradiation lens 1004 is controlled by an irradiation lens control device 1012. The objective lens 1006 is controlled by an objective lens control device 1013. The magnifying lens system 1007 is controlled by a magnifying lens system control device 1014. A control mechanism 1005 of the sample holder is controlled by a holder control device 1015 that controls a drive mechanism of the sample holder.

The electron beam 1003 transmitted through the sample S is detected by the radiation detector 1100. The output signal from the radiation detector 1100 is processed by a signal processing device 1016 and an image processing device 1018 to generate an image signal. The generated image signal (transmission electronic image) is displayed on an image display monitor 1020 and an analysis monitor 1021 as display devices.

Each of the electron beam source control device 1011, the irradiation lens control device 1012, the objective lens control device 1013, the magnifying lens system control device 1014, and the holder control device 1015 is connected to the image processing device 1018. As a result, data can be exchanged with each other in order to set photographing conditions of the electron microscope. The drive control of the sample holder and the observation conditions of each lens can be set by the signal from the image processing device 1018.

An operator prepares the sample S to be photographed and sets photographing conditions using an input device 1019 connected to the image processing device 1018. Predetermined data is input to each of the electron beam source control device 1011, the irradiation lens control device 1012, the objective lens control device 1013, and the magnifying lens system control device 1014, and a desired acceleration voltage, magnification, and observation mode are obtained. In addition, the operator inputs conditions such as the number of continuous visual field images, a photographing start position, and a moving speed of the sample holder to the image processing device 1018 using the input device 1019 such as a mouse, a keyboard, and a touch panel. The specification may be such that the image processing device 1018 automatically sets conditions regardless of the input of the operator.

In the transmission electron microscope (TEM) system of the present embodiment including the radiation detector according to any one of Embodiments 1 to 6, even if the radiation detector is cooled at the time of image capturing, it is possible to effectively prevent application of an excessive force to the thin semiconductor layer having weak mechanical strength due to the imbalance of thermal contraction of each part. Therefore, it is possible to realize a transmission electron microscope (TEM) system which is excellent in reliability and durability and can obtain a captured image with high image quality.

Note that the electron microscope according to the embodiment is not limited to the exemplified transmission electron microscope (TEM) and may be, for example, a scanning electron microscope (SEM) or a scanning transmission electron microscope (STEM). Furthermore, for example, an electron microscope having a processing function such as ion beam milling or ion beam induced deposition (IBID) or a dual-beam electron microscope having a focused ion beam (FIB) such as FIB-SEM may be used.

Modifications of Embodiments

Note that the present invention is not limited to the embodiments described above, and many modifications can be made within the technical idea of the present invention. For example, the different embodiments described above may be implemented in combination.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-80622, filed May 17, 2022, and Patent Application No. 2023-31514, filed Mar. 2, 2023, which are hereby incorporated by reference herein in their entirety.

What is claimed is:

1. A radiation detector comprising:
a semiconductor layer;
a circuit board; and
a heat conduction member,
wherein a first area in which the semiconductor layer and the heat conduction member overlap each other in this order, and the circuit board does not overlap, and a second area in which the semiconductor layer, the circuit board, and the heat conduction member overlap each other in this order are provided adjacent to each other in a case where the radiation detector is seen through from a direction perpendicular to a main surface of the semiconductor layer,
the first area is provided with a space separating the semiconductor layer and the heat conduction member in the direction perpendicular to the main surface at a boundary portion with the second area, and
a height of the space in the direction perpendicular to the main surface of the semiconductor layer is larger than a thickness of the circuit board.

2. The radiation detector according to claim 1,
wherein a linear expansion coefficient of the circuit board is larger than a linear expansion coefficient of the heat conduction member, and the heat conduction member is connected to a cooling device.

3. The radiation detector according to claim 1,
wherein the semiconductor layer is provided with a light receiving portion that receives radiation in the first area.

4. The radiation detector according to claim 3,
wherein a signal processing circuit is provided around the light receiving portion in the semiconductor layer.

5. The radiation detector according to claim 1,
wherein a width of the space is 20 μm or more in a direction parallel to the main surface of the semiconductor layer.

6. The radiation detector according to claim 1,
wherein the semiconductor layer and the heat conduction member are connected via an adhesive layer in at least a part of the first area.

7. The radiation detector according to claim 1,
wherein the semiconductor layer and the heat conduction member are connected via a buffer member in at least a part of the first area.

8. The radiation detector according to claim 7,
wherein the buffer member is a pseudoplastic fluid.

9. The radiation detector according to claim 1,
wherein the circuit board and the semiconductor layer are connected via an adhesive layer in at least a part of the second area.

10. The radiation detector according to claim 1,
wherein the circuit board and the heat conduction member are connected via an adhesive layer in at least a part of the second area.

11. The radiation detector according to claim 1,
wherein the heat conduction member is provided with at least a part of a communication path configured to communicate the space with an external space.

12. The radiation detector according to claim 1,
wherein a buffer member is disposed in the space.

13. A radiation image capturing system comprising:
the radiation detector according to claim 1; and
a signal processing unit configured to process a signal output from the radiation detector.

14. A radiation image capturing system comprising:
the radiation detector according to claim 1; and
a radiation source.

\* \* \* \* \*